US007311899B2

(12) United States Patent
Yu

(10) Patent No.: US 7,311,899 B2
(45) Date of Patent: Dec. 25, 2007

(54) COMPOSITIONS COMPRISING AT LEAST ONE SILICONE, AT LEAST ONE COMPOUND COMPRISING AT LEAST ONE ESTER GROUP, AND AT LEAST ONE COPOLYMER, AND METHODS FOR USING THE SAME

(75) Inventor: Wei Yu, Edison, NJ (US)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/356,523

(22) Filed: Feb. 3, 2003

(65) Prior Publication Data

US 2003/0191244 A1 Oct. 9, 2003
US 2004/0192845 A9 Sep. 30, 2004

Related U.S. Application Data

(60) Provisional application No. 60/353,182, filed on Feb. 4, 2002.

(51) Int. Cl.
*A61Q 5/00* (2006.01)

(52) U.S. Cl. .................. 424/70.12; 526/279; 525/101; 525/104; 525/100

(58) Field of Classification Search ............. 424/70.12; 526/279; 525/100, 101, 104, 474; 524/588
See application file for complete search history.

(56) References Cited

U.S. PATENT DOCUMENTS

| 4,693,935 | A |   | 9/1987  | Mazurek |       |
|-----------|---|---|---------|---------|-------|
| 4,725,658 | A |   | 2/1988  | Thayer et al. |  |
| 4,972,037 | A |   | 11/1990 | Garbe et al. |   |
| 4,981,902 | A |   | 1/1991  | Mitra et al. |   |
| 4,981,903 | A |   | 1/1991  | Garbe et al. |   |
| 5,061,481 | A |   | 10/1991 | Suzuki et al. |  |
| 5,209,924 | A |   | 5/1993  | Garbe et al. |   |
| 5,219,560 | A |   | 6/1993  | Suzuki et al. |  |
| 5,262,087 | A |   | 11/1993 | Tachibana et al. |  |
| 5,334,737 | A |   | 8/1994  | Thimineur et al. |  |
| 5,468,477 | A |   | 11/1995 | Kumar et al. |  |
| 5,567,428 | A |   | 10/1996 | Hughes |   |
| 5,622,694 | A | * | 4/1997  | Torgerson et al. | 424/70.122 |
| 5,665,337 | A | * | 9/1997  | Carballada et al. | 424/70.12 |
| 5,725,845 | A |   | 3/1998  | Krog et al. |  |
| 5,843,418 | A | * | 12/1998 | Coffindaffer et al. | 424/70.11 |
| 5,849,275 | A |   | 12/1998 | Calello et al. |  |
| 5,916,547 | A | * | 6/1999  | Torgerson et al. | 424/70.12 |
| 5,945,092 | A |   | 8/1999  | Krog et al. |  |
| 5,989,533 | A | * | 11/1999 | Deegan et al. | 424/70.28 |
| 6,033,650 | A |   | 3/2000  | Calello et al. |  |
| 6,045,782 | A |   | 4/2000  | Krog et al. |  |
| 6,143,286 | A | * | 11/2000 | Bhambhani et al. | 424/70.1 |
| 6,162,421 | A | * | 12/2000 | Ordino et al. | 424/64 |
| 6,254,876 | B1 |  | 7/2001  | de la Poterie et al. |  |
| 6,254,877 | B1 |  | 7/2001  | de la Poterie et al. |  |
| 6,264,934 | B1 |  | 7/2001  | Kantner et al. |  |
| 6,361,782 | B1 |  | 3/2002  | Chevalier et al. |  |
| 6,361,783 | B2 | * | 3/2002 | Moaddel et al. | 424/401 |
| 6,534,047 | B1 | * | 3/2003 | Bodelin | 424/70.7 |
| 6,555,117 | B2 | * | 4/2003 | Midha et al. | 424/401 |
| 6,620,417 | B1 | * | 9/2003 | Jose et al. | 424/401 |
| 6,682,749 | B1 | * | 1/2004 | Potechin et al. | 424/401 |
| 6,696,049 | B2 | * | 2/2004 | Vatter et al. | 424/63 |
| 2002/0136745 | A1 | * | 9/2002 | Calello et al. | 424/401 |
| 2003/0049212 | A1 | * | 3/2003 | Robinson et al. | 424/59 |
| 2003/0082129 | A1 | * | 5/2003 | Buckingham et al. | 424/70.12 |

FOREIGN PATENT DOCUMENTS

| EP | 0 923 927 | 6/1999 |
| EP | 1 044 673 | 10/2000 |
| EP | 0 602 905 B1 | 6/2002 |
| JP | 10-208305 | 2/2000 |
| WO | WO 93/23446 | 11/1993 |
| WO | WO 95/06078 | 3/1995 |
| WO | WO 01/32727 A1 | 5/2001 |

OTHER PUBLICATIONS

U.S. Appl. No. 60/310,613, Buckingham et al. Aug. 7, 2001.*
Material Safety Data Sheet for Hexyl Alcohol, from jtbaker.com.*
Material Safety Data Sheet for Mineral Oil, from jtbaker.com.*
European Search Report for EP 03 25 0670, mailed Jun. 27, 2005.

* cited by examiner

*Primary Examiner*—Margaret G. Moore
(74) *Attorney, Agent, or Firm*—Finnegan, Henderson, Farabow, Garrett & Dunner LLP

(57) ABSTRACT

Compositions, and methods for using compositions, comprising at least one silicone, at least one compound comprising at least one ester group, and at least one copolymer. In an embodiment, the inventive compositions do not comprise any volatile solvents. Compositions comprising at least one encapsulated pigment, wherein the at least one encapsulated pigment is dispersed in at least one silicone are also disclosed.

18 Claims, No Drawings

COMPOSITIONS COMPRISING AT LEAST ONE SILICONE, AT LEAST ONE COMPOUND COMPRISING AT LEAST ONE ESTER GROUP, AND AT LEAST ONE COPOLYMER, AND METHODS FOR USING THE SAME

This application is based upon and claims the benefit of priority of U.S. provisional application No. 60/353,182, filed Feb. 4, 2002, the disclosure of which is incorporated herein by reference.

In an embodiment, the present invention relates to compositions, and methods for using compositions, comprising at least one silicone, at least one compound comprising at least one ester group, and at least one copolymer comprising at least one backbone and at least one chain, wherein at least one of the at least one backbone and at least one chain is chosen from silicones. In an embodiment, the inventive compositions do not comprise any volatile solvents.

Cosmetic and/or dermatological products may comprise a structured, i.e., gelled and/or rigidified, liquid fatty phase, such as in solid compositions, for example, deodorants, lip balms, lipsticks, concealer products, eyeshadows, and cast foundations. This structuring may be obtained with the aid of waxes and/or fillers. Unfortunately, these waxes and fillers may have a tendency to make the composition matte, which may not always be desirable, in particular for a lipstick or an eyeshadow. Specifically, consumers may be interested in a lipstick in stick form which has at least one of the following properties: depositing a film with good staying power and/or long wearing properties, glossiness, and wear comfort.

Gloss of a lipstick or other cosmetic is generally associated with the nature of the liquid fatty phase. Thus, it may be possible to reduce the amount of waxes and/or fillers in the composition to increase the gloss of a lipstick, often, however, that leads to an increase in the migration of the liquid fatty phase. In other words, the amounts of waxes and of fillers required to prepare a stick of suitable hardness which does not exude at room temperature are usually a restricting factor on the gloss of the deposit.

Furthermore, it is desirable that care, treatment, and make-up compositions have good staying power or long wearing properties over time. Poor staying power is characterized by a color change (turning, fading) or a non-uniform change in the make-up effect over time, generally following an interaction with sebum and/or sweat secreted by the skin, and, for the lips, an interaction with saliva. Specifically, a composition which does not have good staying power or long-wearing properties over time may oblige the user to reapply the make-up regularly. However, consumers nowadays often wish to enhance the beauty of their face or body while spending as little time as possible in doing so. Finally, it is often desirable that a care or make-up composition be comfortable to wear, for example, non-desiccating and not tightening.

To overcome at least one of these drawbacks, the inventors, in an embodiment of the invention, have envisaged replacing all or some of the waxes and/or fillers with at least one compound comprising at least one ester group, at least one silicone, and at least one copolymer comprising at least one backbone and at least one chain, wherein at least one of the at least one backbone and at least one chain is chosen from silicones.

In an embodiment, the present invention provides a composition comprising at least one compound comprising at least one ester group, at least one silicone, and at least one copolymer comprising at least one backbone and at least one chain, wherein at least one of the at least one backbone and at least one chain is chosen from silicones, with the proviso that the composition comprises no volatile solvents. In an embodiment, the inventive composition further comprises at least one wax that is not a compound comprising at least one ester group. In another embodiment, the at least one copolymer structures the liquid fatty phase of the composition.

In an embodiment, the inventive compositions do not comprise any volatile solvents. In an embodiment, the inventive compositions are stable. In another embodiment, the at least one copolymer is chosen from copolymers comprising at least one polar backbone and at least one non-polar chain and copolymers comprising at least one non-polar backbone and at least one polar chain, wherein at least one of the at least one backbone and at least one chain is chosen from silicones. In another embodiment, the at least one compound comprising at least one ester group and, if present, the at least one wax are incompatible with the at least one silicone.

The at least one copolymer may make it possible to stabilize a composition, such as a composition in the form of a stick, which comprises at least one compound comprising at least one ester group, such as at least one ester and/or at least one diester, at least one silicone, and optionally at least one wax not comprising at least one ester group, wherein the at least one compound and, if present, the at least one wax are incompatible with the at least one silicone.

Accordingly, the inventive composition may make it possible, in addition to obtaining a product in the form of a stick or tube, to limit the exudation of a fatty phase from solid compositions, especially in hot and humid regions, and/or to limit, after deposition on keratinous material, such as skin or lips, the migration of this phase into wrinkles and fine lines. These characteristics are particularly sought after in cosmetic compositions, such as concealer products, eyeshadows, and lip products, such as lipsticks. Specifically, large migration of the liquid fatty phase, in particular when it is charged with coloring agents, may lead to an unpleasant appearance around the lips and the eyes, which particularly makes the wrinkles and fine lines more prominent. This migration is often mentioned by consumers as being a major defect of conventional lip products, concealer products and eye make-ups.

Accordingly, in an embodiment, the present invention is drawn to a care and/or make-up and/or treatment composition for the skin and/or the lips of the face and/or for superficial body growths, such as keratinous fibres, such as hair, which may make it possible to overcome at least one of the drawbacks mentioned above comprising at least one silicone, at least one compound comprising at least one ester group, and at least one copolymer comprising at least one backbone and at least one chain, wherein at least one of the at least one backbone and at least one chain is chosen from silicones.

The compositions of the present invention can be stable over time and may be in the form of a make-up stick, such as lipstick. Further, application of the inventive composition on keratinous material may produce a glossy, migration-resistant deposit, such as a layer, and may possess good staying power and/or long-wearing properties without being uncomfortable to the wearer.

The present invention, in an embodiment, provides an anhydrous composition comprising at least one diester, at least one silicone, and at least one copolymer comprising at least one backbone and at least one chain, wherein at least one of the at least one backbone and at least one chain is chosen from silicones. In an embodiment, the inventive composition does not comprise any volatile solvents. In an embodiment, the inventive composition is a cosmetic composition. In an embodiment, the inventive composition further comprises at least one wax not chosen from diesters.

In another embodiment, the present invention provides a composition comprising at least one diester of formula (I), at least one silicone, and at least one copolymer comprising at least one backbone and at least one chain, wherein at least one of the at least one backbone and at least one chain is chosen from silicones. The at least one diester of formula (1) has the following structure:

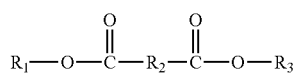

(I)

wherein $R_1$ and $R_3$, which may be identical or different, are each chosen from optionally substituted hydrocarbon groups; and $R_2$ is chosen from optionally substituted, divalent hydrocarbon groups. In another embodiment, $R_2$ is not a phenyl group. In another embodiment, the at least one diester of formula (I) is not dibutyl phthalate. In another embodiment, the composition does not comprise any volatile solvents. In another embodiment, the composition further comprises at least one wax not chosen from diesters of formula (I). In another embodiment, the inventive composition is a cosmetic composition.

In another embodiment, the present invention provides a composition comprising at least one diester, at least one ester of formula (II), at least one silicone, and at least one copolymer comprising at least one backbone and at least one chain, wherein at least one of the at least one backbone and at least one chain is chosen from silicones. The at least one ester of formula (II) has the following structure:

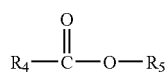

(II)

wherein $R_4$ and $R_5$, which may be identical or different, are each chosen from unsubstituted hydrocarbon groups, wherein the hydrocarbon groups each comprise at least four carbon atoms, and in particular, at least eight carbon atoms, and further, for example, at least ten carbon atoms.

In an embodiment, the at least one diester is chosen from diesters of formula (I). In an embodiment, the composition further comprises at least one wax not chosen from diesters and esters of formula (II). In an embodiment, the composition does not comprise any volatile solvents. In another embodiment, the inventive composition is a cosmetic composition.

In another embodiment, the present invention provides a composition comprising at least two compounds chosen from diesters and esters of formula (II) discussed above, at least one silicone, and at least one copolymer comprising at least one backbone and at least one chain, wherein at least one of the at least one backbone and at least one chain is chosen from silicones. In an embodiment, the at least two compounds are present in the inventive composition in an amount greater than or equal to 3.5% by weight relative to the total weight of the composition. In an embodiment, the composition does not comprise any volatile solvents. In another embodiment, the composition further comprises at least one wax not chosen from diesters and esters of formula (II). In an embodiment, the inventive composition is a cosmetic composition.

In another embodiment, the present invention provides a method for modifying the structure of a composition which comprises at least one silicone and at least one compound comprising at least one ester group, wherein the at least one silicone and the at least one compound are incompatible, comprising including in the composition at least one copolymer comprising at least one backbone and at least one chain, wherein at least one of the at least one backbone and at least one chain is chosen from silicones in an amount effective to provide a stable composition. In an embodiment, the composition does not comprise any volatile solvents. In another embodiment, the composition further comprises at least one wax not comprising at least one ester group. In another embodiment, the inventive composition is a cosmetic composition.

In another embodiment, the present invention is drawn to a method for making a stable anhydrous composition comprising adding to the composition at least one diester, at least one silicone, and at least one copolymer comprising at least one backbone and at least one chain, wherein at least one of the at least one backbone and at least one chain is chosen from silicones, wherein the at least one copolymer is present in an amount effective to provide a stable composition. In an embodiment, the composition does not comprise any volatile solvents. In another embodiment, the composition further comprises at least one wax not chosen from diesters. In another embodiment, the inventive composition is a cosmetic composition.

In another embodiment, the present invention is drawn to a method for making a stable composition comprising adding to the composition at least one diester of formula (I), at least one silicone, and at least one copolymer comprising at least one backbone and at least one chain, wherein at least one of the at least one backbone and at least one chain is chosen from silicones, wherein the at least one copolymer is present in an amount effective to provide a stable composition. In an embodiment, the composition does not comprise any volatile solvents. In another embodiment, the composition further comprises at least one wax not chosen from diesters of formula (I). In another embodiment, the inventive composition is a cosmetic composition.

In another embodiment, the present invention is drawn to a method for making a stable composition comprising adding to the composition at least one diester, at least one ester of formula (II), at least one silicone, and at least one copolymer comprising at least one backbone and at least one chain, wherein at least one of the at least one backbone and at least one chain is chosen from silicones, wherein the at least one copolymer is present in an amount effective to provide a stable composition. In an embodiment, the composition does not comprise any volatile solvents. In another embodiment, the composition further comprises at least one wax not chosen from diesters and esters of formula (II). In another embodiment, the inventive composition is a cosmetic composition.

In another embodiment, the present invention is drawn to a method for making a stable composition comprising adding to the composition at least two compounds chosen from diesters and esters of formula (II), discussed above, at least one silicone, and at least one copolymer comprising at least one backbone and at least one chain, wherein at least one of the at least one backbone and at least one chain is chosen from silicones, wherein the at least one copolymer is present in an amount effective to provide a stable composition. In an embodiment, the at least two esters are present in the inventive composition in an amount greater than or equal to 3.5% by weight relative to the total weight of the composition. In an embodiment, the composition does not comprise any volatile solvents. In another embodiment, the composition further comprises at least one wax not chosen from diesters and esters of formula (II). In an embodiment, the inventive composition is a cosmetic composition.

In another embodiment, the present invention provides a method for caring for, making up and/or treating at least one keratinous material comprising applying to the at least one keratinous material an anhydrous composition comprising at least one diester, at least one silicone, and at least one copolymer comprising at least one backbone and at least one chain, wherein at least one of the at least one backbone and at least one chain is chosen from silicones. In an embodiment, the composition does not comprise any volatile solvents. In another embodiment, the composition further comprises at least one wax not chosen from diesters. In another embodiment, the at least one copolymer is present in an amount effective to provide a stable composition.

In another embodiment, the present invention provides a method for caring for, making up and/or treating at least one keratinous material comprising applying to the at least one keratinous material a composition comprising at least one diester of formula (I), at least one silicone, and at least one copolymer comprising at least one backbone and at least one chain, wherein at least one of the at least one backbone and at least one chain is chosen from silicones. In another embodiment, the at least one copolymer is present in an amount effective to provide a stable composition. In another embodiment, the composition does not comprise any volatile solvents. In another embodiment, the composition further comprises at least one wax not chosen from diesters of formula (I).

In another embodiment, the present invention provides a method for caring for, making up and/or treating at least one keratinous material comprising applying to the at least one keratinous material a composition comprising at least one diester and at least one ester of formula (II), at least one silicone, and at least one copolymer comprising at least one backbone and at least one chain, wherein at least one of the at least one backbone and at least one chain is chosen from silicones. In another embodiment, the at least one copolymer is present in an amount effective to provide a stable composition. In another embodiment, the composition does not comprise any volatile solvents. In another embodiment, the composition further comprises at least one wax not chosen from diesters and esters of formula (II).

In another-embodiment, the present invention provides a method for caring for, making up and/or treating at least one keratinous material comprising applying to the at least one keratinous material a composition comprising at least two compounds chosen from diesters and esters of formula (II), discussed above, at least one silicone, and at least one copolymer comprising at least one backbone and at least one chain, wherein at least one of the at least one backbone and at least one chain is chosen from silicones. In an embodiment, the at least two compounds are present in the inventive composition in an amount greater than or equal to 3.5% by weight relative to the total weight of the composition. In another embodiment, the composition does not comprise any volatile solvents. In another embodiment, the at least one copolymer is present in an amount effective to provide a stable composition. In another embodiment, the composition further comprises at least one wax not chosen from diesters and esters of formula (II).

Certain terms used herein are defined below:

"At least one" means one or more and thus includes individual components as well as mixtures/combinations.

"Anhydrous," as used herein, refers to compositions comprising less than 5% water by weight relative to the total weight of the composition, such as less than 2% water by weight, and further such as less than 1% water by weight. The amount of water in the composition for purposes of this invention refers to the amount of water added to the components of the composition.

"Backbone," as used herein, refers to the skeleton of a polymer.

A "chain," as used herein, refers to a group chosen from optionally substituted hydrocarbon groups and groups comprising at least one functional group. Further, a "chain" may be located at at least one position chosen from terminal, i.e., at at least one end of the polymer backbone, and pendant, with respect to the polymer backbone.

"Gloss," as used herein, refers to surface shininess. The gloss of a composition may, for example, be measured and evaluated using a gloss meter. Gloss meters are commonly used in the nail polish art, and measure the amount of light reflected from the surface or film of interest. The gloss may be quantified, for example, as a % reflectance.

"Hydrocarbons," as used herein, includes substituted linear alkyl groups, unsubstituted linear alkyl groups, substituted branched alkyl groups, unsubstituted branched alkyl groups, substituted cyclic alkyl groups, unsubstituted cyclic alkyl groups, linear alkenyl groups, unsubstituted linear alkenyl groups, substituted branched alkenyl groups, unsubstituted branched alkenyl groups, substituted cyclic alkenyl groups, unsubstituted cyclic alkenyl groups, substituted aromatic groups, and unsubstituted aromatic groups, wherein the aforementioned groups comprise only carbon and hydrogen atoms.

"Substituted," as used herein, means further comprising at least one substituent. Non-limiting examples of substituents include atoms, such as oxygen, nitrogen, and halogens, as well as functional groups, such as hydroxyl, ether groups, oxyalkylene groups, polyoxyalkylene groups, carboxylic acid groups, amine groups, and amide groups.

"Liquid fatty phase," as used herein, means a fatty phase which is liquid at room temperature (25° C.) and atmospheric pressure (760 mmHg), and comprises at least one fatty substance (also referred to as an oil) that is liquid at room temperature and atmospheric pressure.

"Fatty substance," such as liquid fatty substance, means a nonaqueous medium which is immiscible in all proportions with water, for example, a hydrocarbon-based compound comprising at least one carbon chain containing at least 5 carbon atoms and possibly comprising at least one polar group chosen from carboxylic acid groups, hydroxyl, polyol groups, amine groups, amide groups, phosphoric acid groups, phosphate groups, ester groups, ether groups, urea groups, carbamate groups, thiol groups, thioether groups, and thioester groups; a silicone compound optionally comprising carbon chains at the end and/or pendant, these chains optionally being substituted with at least one group chosen from fluoro groups, perfluoro groups, (poly)amino acid groups, ether groups, hydroxyl, amino groups, acid groups, and ester groups; or a fluoro and/or perfluoro compound such as fluorohydrocarbons or perfluorohydrocarbons containing at least 5 carbon atoms, possibly comprising at least one hetero atom chosen from N, O, S and P and optionally comprising at least one polar group chosen from ether groups, ester groups, amine groups, acid groups, carbamate groups, urea groups, thiol groups, and hydroxyl.

"Incompatible" compounds, as used herein, refers to compounds which, when combined in the absence of the at least one copolymer, result in a composition which is not homogeneous as viewed by the naked eye. For example, compounds are incompatible when, after a composition comprising the compounds is heated with mixing to a temperature which is equal to the melting point of highest melting compound in the composition and after 5 minutes without mixing but while maintaining the temperature, the composition is cloudy to the naked eye and/or comprises at least two separate phases as viewed by the naked eye.

"Migration," as used herein, means a running of the composition beyond the initial application line as viewed by the naked eye.

"Keratinous fibers," as used herein, includes hair (including eyelashes and eyebrows).

"Keratinous material," as used herein, includes skin (including lips), hair (including eyelashes and eyebrows), and nails.

"Polymer," as used herein, comprises copolymers and homopolymers, including but not limited to, for example, block polymers, cross linked polymers, and graft polymers.

"Copolymer," as used herein, refers to polymers formed from at least two different types of monomers.

"Silicone" as used herein, includes, for example, silica, silanes, silazanes, siloxanes, organosilanes and organosiloxanes; and refers to a compound comprising at least one silicon atom; wherein the silicone may be chosen from linear silicones, branched silicones, and cyclic silicones; further wherein the silicone may optionally be substituted; further wherein the silicone may optionally further comprise at least one heteroatom intercalated in the silicone chain, wherein the at least one heteroatom is different from the at least one silicon atom.

"Volatile solvent," as used herein, refers to an aqueous or nonaqueous medium which is liquid at room temperature (25° C.) and at atmospheric pressure (760 mmHg) and which has a vapor pressure greater than 2 mmHg (at room temperature and atmospheric pressure). Phenyl trimethicone is not a volatile solvent.

"Nonvolatile" compounds, as used herein, refers to nonaqueous compounds which are liquid at room temperature and atmospheric pressure and which have a vapor pressure up to and including 2 mmHg (at room temperature and atmospheric pressure). Phenyl trimethicone is a nonvolatile compound.

It is to be understood that both the foregoing general description and the following detailed description are exemplary and explanatory only and are not restrictive of the invention as claimed. Reference will now be made in detail to exemplary embodiments of the present invention.

The invention applies not only to make-up products for the lips, such as lipsticks, lip glosses and lip pencils, but also to care and/or treatment products for the skin, including the scalp, and for the lips, such as antisun products, for example in stick form for facial skin or the lips, care products for the human face or body, make-up products for the skin, both of the human face and body, such as foundations optionally cast in stick or dish form, concealer products, blushers, make-up removing products, eyeshadows, face powders, transfer tattoos, body hygiene products such as deodorants, e.g., in stick form, shampoos, conditioners and make-up products for the eyes such as eyeliners, eye pencils and mascaras, e.g., in stick form, as well as make-up and care products for superficial body growths, for instance keratinous fibers such as the hair, the eyelashes and the eyebrows.

The use of at least one specific copolymer in the presence of at least one compound comprising at least one ester group and at least one silicone, such as in the liquid fatty phase of a composition, may make it possible to obtain a composition in rigid form such as a stick, whose application to the skin or the lips produces a deposit which has at least one noteworthy cosmetic property. For example, the deposit may be at least one of glossy, supple, comfortable, light, "migration-resistant," and having staying power and/or long-wearing properties.

Moreover, the composition may be stable over time, may withstand shear during application and/or may not exude at room temperature. In addition, the structuring of the fatty phase of the composition may produce a product that is easy to handle since it does not run between the fingers, unlike a liquid product. In an embodiment, the at least one copolymer is present in an amount effective to provide a stable composition.

The term "stable" refers to a composition which, under prescribed conditions, does not exhibit at least one abnormality in the composition such as, for example, bending or leaning if the composition is in stick form, phase separation, melting, or syneresis.

Stability may be tested by placing the composition in a controlled environment chamber for a specific amount of time at a specific temperature. Compositions in the form of a stick are tested standing up in the chamber. "Standing up," as used herein, means upright, in a vertical position. For example, if the composition is in the form of a stick, the stick is placed upright in the chamber, i.e., in a vertical position with respect to the surface of the chamber on which the stick is placed.

In an embodiment, a composition is stable if it does not exhibit at one least abnormality in the composition after 2 months at room temperature (25° C.) as viewed by the naked eye. In another embodiment, a composition is stable if it does not exhibit at least one abnormality in the composition after 6 months at room temperature (25° C.) as viewed by the naked eye. In another embodiment, a composition is stable if it does not exhibit at least one abnormality in the composition after 9 months at room temperature (25° C.) as viewed by the naked eye. In another embodiment, a composition is stable if it does not exhibit at least one abnormality in the composition after 4 weeks at 37° C. as viewed by the naked eye. In another embodiment, a composition is stable if it does not exhibit at least one abnormality in the composition after 4 weeks at 50° C. as viewed by the naked eye.

In these stability tests, the physical condition of the sample is inspected as it is placed in the chamber. The sample is then inspected after a specific length of time after the sample is placed in the chamber, such as 8 hours, 12 hours, 24 hours, 1 week, 2 weeks, 3 weeks, 4 weeks, 5 weeks, 6 weeks, 7 weeks, 8 weeks (2 months), 12 weeks (3 months), 16 weeks (4 months), 20 weeks (5 months), 24 weeks (6 months), 28 weeks (7 months), 32 weeks (8 months), 36 weeks (9 months), and/or 56 weeks (1 year). The temperature of the chamber is set at a specific temperature, such as 25° C., 37° C., or 50° C., as described above, or, as further examples, at 4° C. for 1 year, or at 45° C. for 4 weeks.

In another embodiment, a sample is tested for at least one abnormality under freeze-thaw conditions, where the sample is frozen for 12 hours and then allowed to thaw for 12 hours. Generally, freeze-thaw conditions comprise 3 cycles of each of the aforementioned 12 hour periods.

At each inspection, the sample is examined for at least one abnormality in the composition such as, for example, bending or leaning if the composition is in stick form, phase separation, melting, or syneresis. As used herein, "syneresis" is the appearance of droplets on a surface of a composition that are visible to the naked eye.

The skilled artisan will readily recognize at least one abnormality that impedes functioning of a composition based on the intended application, such as, for example, the appearance of at least one abnormality as described above. The skilled artisan will also readily recognize that the observation of at least one abnormality that impedes functioning of a composition will depend not only on its intended application, but its composition as well.

In an embodiment, the invention is drawn to a composition comprising at least one liquid fatty phase which comprises at least one compound comprising at least one ester group and at least one silicone, wherein the at least one compound is incompatible with the at least one silicone, and at least one copolymer comprising at least one backbone and at least one chain, wherein at least one of the at least one backbone and at least one chain is chosen from silicones.

In one aspect, the present invention is drawn to a structured composition-comprising at least one liquid fatty phase structured with at least one copolymer chosen from copolymers comprising a polymer skeleton comprising at least one non-polar, silicone backbone substituted with at least one polar non-silicone chain and copolymers comprising a polymer skeleton comprising at least one polar, non-silicone backbone substituted with at least one non-polar, silicone chain, wherein the at least one liquid fatty phase comprises at least one compound comprising at least one ester group and at least one silicone. The at least one liquid fatty phase, the at least one copolymer, the at least one compound, and the at least one silicone form a physiologically acceptable medium.

The composition of the invention can be in the form of a paste, a solid, a viscous cream, a rigid gel, or flexible gel. It can be a single or multiple emulsion, such as an oil-in-water or water-in-oil emulsion or an oil-in-water-in-oil emulsion, or a water-in-oil-in-water emulsion, or a rigid or soft gel containing an oily continuous phase. For example, the liquid fatty phase can be the continuous phase of the composition. In an embodiment, the composition is in a form cast as a stick or in a dish, for example, in the form of an oily rigid gel, such as an anhydrous gel, e.g., an anhydrous stick. In a further embodiment, the composition is in the form of an opaque or translucent rigid gel (depending on the presence or absence of pigments), and in another embodiment, the liquid fatty phase forms the continuous phase. In another embodiment, the composition of the invention is self-supporting. In another embodiment, the composition of the invention is an anhydrous composition.

The at least one liquid fatty phase may be modified according to the nature of the at least one copolymer, of the at least one compound comprising at least one ester group, and of the at least one silicone used, and may be such that a rigid structure in the form of a tube or stick with mechanical strength is obtained. When these tubes or sticks are colored, they may make it possible, after application, to obtain a uniformly, i.e., homogeneously, colored glossy deposit, such as a layer, which does not migrate, for example, into the wrinkles and fine lines of the skin surrounding, for example, the lips and eyes, and which has good staying power and/or long-wearing properties, in particular of the color, over time.

The composition of the invention may, for example, be a composition for the skin or the lips, such as a foundation composition, concealer product, eyeshadow or lipstick composition, e.g., in stick form.

According to the present invention, the at least one silicone may be chosen from water-soluble silicones, oil soluble silicones, and silicones which are soluble in organic solvents. In an embodiment, the at least one silicone is chosen from linear nonvolatile silicones, branched nonvolatile silicones, and cyclic nonvolatile silicones.

Non-limiting examples of the at least one silicone according to the present invention include dimethicones (polydimethylsiloxanes), trimethicones, polyalkyl siloxanes, polyaryl siloxanes, polyalkylaryl siloxanes, polyether siloxane copolymers, alkylaryl-diaryl siloxane copolymers, dimethiconols, polydialkylsiloxane/alkylvinylsiloxane copolymers, (polydialkylsiloxane)(diphenyl)(methylvinylsiloxane) copolymers, and silicone resins (siloxysilicates). In one embodiment, the at least one silicone is chosen from trimethicones. In another embodiment, the at least one silicone is phenyltrimethicone.

In an embodiment, the at least one silicone is chosen from siloxysilicates. In one embodiment, the at least one silicone is chosen from phenylpropyldimethylsiloxysilicate. Phenylpropyldimethylsiloxysilicate is commercially available, for example, from GE under the tradename Baysilone CF-1301. In one embodiment, the siloxysilicate is trimethylsiloxysilicate. Trimethylsiloxysilicate (TMS) is commercially available from GE under the tradename SR1000 and from Wacker under the tradename TMS 803. Further, the trimethylsiloxysilicate may be in the form of a powder. TMS is commercially available, for example, from Dow Chemical, in a solvent, such as for example, cyclomethicone. However, according to the present invention, TMS may be used in the form of 100% active material, that is, not in a solvent. In an embodiment, the at least one silicone does not comprise at least one solvent. In another embodiment, the at least one silicone does not comprise at least one volatile solvent. In another embodiment, the at least one silicone is trimethysiloxysilicate, wherein the at least one silicone does not further comprise at least one solvent.

Other non-limiting examples of at least one silicone suitable for use in the present invention are cyclopentasiloxane and stearyl dimethicone silicate crosspolymers.

In an embodiment, the at least one silicone is present in the composition in an amount ranging from 0.5% to 20% by weight relative to the total weight of the composition. In another embodiment, the at least one silicone is present in an amount ranging from 1% to 10% by weight relative to the total weight of the composition. As discussed above, the at least one silicone according to the present invention may be commercially available, and may come from suppliers in the form of a dilute solution. The amounts of the at least one silicone disclosed herein therefore reflect the weight percent of active material.

As discussed above, the inventive compositions may comprise at least one silicone which does not further comprise at least one solvent. Accordingly, the present invention, in an embodiment, provides a method of making a composition comprising including in the composition at least one silicone which does not further comprise at least one solvent. In an embodiment, the at least one solvent is chosen from volatile solvents. In another embodiment, the at least one silicone is trimethysiloxysilicate. In an embodiment, the present invention provides a method of making a composition comprising including in the composition at least one silicone chosen from trimethysiloxysilicate, wherein the at least one silicone does not further comprise at least one solvent.

According to the present invention, the inventive compositions, in certain embodiments, comprise at least one diester. As defined herein, the term "diester" refers to a molecule comprising two, and only two, ester groups. Thus, non-limiting examples of at least one diester include diesters of formula (I):

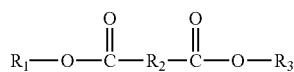

(I)

and diesters of the following formula:

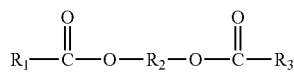

wherein $R_1$ and $R_3$, which may be identical or different, are each chosen from optionally substituted hydrocarbon groups; and $R_2$ is chosen from optionally substituted, divalent hydrocarbon groups. In an embodiment, $R_2$ is not a phenyl group in formula (I). In another embodiment, the at least one diester of formula (I) is not dibutyl phthalate.

Non-limiting examples of suitable diesters include fatty acid diesters, diesters of alcohols, and PEG diesters. Additional non-limiting examples include diisostearyl malate, diglycerol diisotearate, and PEG distearates. In an embodiment, the at least one diester is chosen from diesters of formula (I). In another embodiment, at least one diester of formula (I) is chosen from diisostearyl malate.

In certain embodiments of the present invention, the compositions comprise at least one compound comprising at least one ester group. As defined herein, the term "ester" refers to a molecule comprising one, and only one, ester group. Thus, non-limiting examples of at least one compound comprising at least one ester group include esters of formula (II):

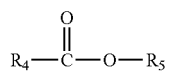

(II)

wherein $R_4$ and $R_5$, which may be identical or different, are each chosen from unsubstituted hydrocarbon groups, wherein the hydrocarbon groups each comprise at least four carbon atoms, and and esters of the following formula:

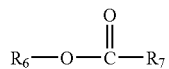

wherein $R_6$ and $R_7$, which may be identical or different, are each chosen from optionally substituted hydrocarbon groups.

Further, according to the present invention, the inventive compositions, in certain embodiments, comprise at least one diester and at least one ester of formula (II), above. Non-limiting examples of at least one ester of formula (II) include butyl heptanoate, butyl laurate, butyl isononanoate, butyl myristate, butyl octanoate, butyl oleate, butyl palmitate, butyl stearate, cetyl heptanoate, cetyl laurate, cetyl isononanoate, cetyl myristate, cetyl octanoate, cetyl oleate, cetyl palmitate, cetyl stearate, isononyl heptanoate, isononyl laurate, isononyl isononanoate, isononyl myristate, isononyl octanoate, isononyl oleate, isononyl palmitate, isononyl stearate, hexyl heptanoate, hexyl laurate, hexyl isononanoate, hexyl myristate, hexyl octanoate, hexyl oleate, hexyl palmitate, hexyl stearate, isostearyl heptanoate, isostearyl isostearate, isostearyl neopentanoate, isostearyl isononanoate, lauryl heptanoate, lauryl isononanoate, lauryl myristate, lauryl octanoate, lauryl oleate, lauryl palmitate, lauryl stearate, stearyl heptanoate, stearyl laurate, stearyl isononanoate, stearyl myristate, stearyl octanoate, stearyl oleate, stearyl palmitate, and stearyl stearate.

One of ordinary skill in the art will recognize that the at least one compound comprising at least one ester group, such as esters and diesters, according to the present invention may be commercially available, and may come from suppliers in the form of a dilute solution. The amounts of these components disclosed herein reflect the weight percent of active material.

In an embodiment, the at least one compound comprising at least one ester group may also be chosen from at least one wax.

In an embodiment, the at least one ester is present in the composition in an amount ranging from 1% to 80% by weight relative to the total weight of the composition. In another embodiment, the at least one ester is present in an amount ranging from 5% to 60% by weight relative to the total weight of the composition.

In an embodiment, the at least one diester is present in the composition in an amount ranging from 1% to 80% by weight relative to the total weight of the composition. In another embodiment, the at least one diester is present in an amount ranging from 5% to 60% by weight relative to the total weight of the composition.

In an embodiment, the at least one compound comprising at least one ester group is present in the composition in an amount ranging from 1% to 80% by weight relative to the total weight of the composition. In another embodiment, the at least one compound comprising at least one ester group is present in an amount ranging from 5% to 60% by weight relative to the total weight of the composition.

The at least one copolymer according to the present invention is different from the at least one silicone and is different from the at least one compound comprising at least one ester group. The at least one copolymer comprises at least one backbone and at least one chain, wherein at least one of the at least one backbone and at least one chain is chosen from silicones. In an embodiment, the at least one copolymer is chosen from copolymers comprising at least one polar backbone and at least one non-polar chain and copolymers comprising at least one non-polar backbone and at least one polar chain, wherein at least one of the at least one backbone and at least one chain is chosen from silicones.

In an embodiment, the at least one copolymer is chosen from copolymers comprising a polymer skeleton comprising at least one non-polar, silicone backbone substituted with at least one polar, non-silicone chain and copolymers comprising a polymer skeleton comprising at least one polar, non-silicone backbone substituted with at least one non-polar, silicone chain.

In another embodiment, the at least one copolymer is chosen from copolymers comprising a polymer skeleton comprising at least one polar, silicone backbone substituted with at least one non-polar, non-silicone chain and copolymers comprising a polymer skeleton comprising at least one non-polar, non-silicone backbone substituted with at least one polar, silicone chain.

In an embodiment, the at least one polar chain comprises at least one ester group. In another embodiment, the at least one polar chain comprises at least one ester group and at least one double bond. In another embodiment, the at least one polar, non-silicone backbone is chosen from acrylate polymers, methacrylate polymers, and vinyl polymers.

In another embodiment, the at least one copolymer further comprises at least one hydrocarbon group. In an embodiment, the at least one hydrocarbon group is a terminal hydrocarbon group bonded to the polymer skeleton. In another embodiment, the at least one hydrocarbon group is a pendant hydrocarbon group bonded to the polymer skeleton. In another embodiment, the at least one hydrocarbon group is a terminal hydrocarbon group bonded to at least one chain on the polymer skeleton. In another embodiment, the hydrocarbon group is a pendant hydrocarbon group bonded to at least one chain on the polymer skeleton. Non-limiting examples of the at least one hydrocarbon group include $C_5$-$C_{25}$ alkyl groups, optionally substituted, such as $C_{18}$ alkyl groups and $C_{22}$ alkyl groups.

Non-limiting examples of the at least one copolymer include silicone/(meth)acrylate copolymers, such as those as described in U.S. Pat. Nos. 5,061,481, 5,219,560, and 5,262,087, the disclosures of which are hereby incorporated by reference. Further non-limiting examples of the at least one copolymer are non-polar silicone copolymers comprising repeating units of at least one polar (meth)acrylate unit and vinyl copolymers grafted with at least one non-polar silicone chain. Non-limiting examples of such copolymers are acrylates/stearyl acrylate/dimethicone acrylates copolymers, such as those commercially available from Shin-Etsu, for example, the product sold under the tradename KP-561, and acrylates/behenyl acrylate/dimethicone acrylates copolymer, such as those commercially available from Shin-Etsu, for example, the product sold under the tradename KP-562.

Another non-limiting example of at least one copolymer suitable for use in the present invention are silicone esters comprising units of formulae (III) and (IV), disclosed in U.S. Pat. Nos. 6,045,782, 5,334,737, and 4,725,658, the disclosures of which are hereby incorporated by reference:

  (III); and

  (IV)

wherein
R and R', which may be identical or different, are each chosen from optionally substituted hydrocarbon groups;

a and b, which may be identical or different, are each a number ranging from 0 to 3, with the proviso that the sum of a and b is a number ranging from 1 to 3, x and y, which may be identical or different, are each a number ranging from 0 to 3, with the proviso that the sum of x and y is a number ranging from 1 to 3;

$R^E$, which may be identical or different, are each chosen from groups comprising at least one carboxylic ester.

In an embodiment, $R^E$ groups are chosen from groups comprising at least one ester group formed from the reaction of at least one acid and at least one alcohol. In an embodiment, the at least one acid comprises at least two carbon atoms. In another embodiment, the at least one alcohol comprises at least ten carbon atoms. Non-limiting examples of the at least one acid include branched acids such as isostearic acid, and linear acids such as behenic acid. Non-limiting examples of the at least one alcohol include monohydric alcohols and polyhydric alcohols, such as n-propanol and branched etheralkanols such as (3,3,3-trimethylolpropoxy)propane.

Further non-limiting examples of the at least one copolymer include liquid siloxy silicates and silicone esters such as those disclosed in U.S. Pat. No. 5,334,737, such as diisostearoyl trimethylolpropane siloxysilicate and dilauroyl trimethylolpropane siloxy silicate, which are commercially available from General Electric under the tradenames SF 1318 and SF 1312, respectively.

Further non-limiting examples of the at least one copolymer include polymers comprising a backbone chosen from vinyl polymers, methacrylic polymers, and acrylic polymers and at least one chain chosen from pendant siloxane groups and pendant fluorochemical groups. Non-limiting examples of such polymers comprise at least one unit derived from at least one A monomer, at least one unit derived from at least one C monomer, at least one unit derived from D monomers, and, optionally, at least one unit derived from at least one B monomer, wherein:

A, which may be identical or different, are each chosen from free-radically-polymerizable acrylic esters of at least one alcohol chosen from 1,1,-dihydroperfluoroalkanols, omega-hydridofluoroalkanols, fluoroalkylsulfonamido alcohols, cyclic fluoroalkyl alcohols, and fluoroether alcohols, and analogs of any of the foregoing at least one alcohols, and free-radically-polymerizable methacrylic esters of at least one alcohol chosen from 1,1,-dihydroperfluoroalkanols, omega-hydridofluoroalkanols; fluoroalkylsulfonamido alcohols, cyclic fluoroalkyl alcohols, and fluoroether alcohols, and analogs of any of the foregoing at least one alcohols;

B, which may be identical or different, are each chosen from reinforcing monomers which are copolymerizable with at least one A monomer;

C, which may be identical or different, are each chosen from monomers having the formula:

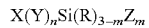

wherein
X is chosen from vinyl groups which are copolymerizable with at least one A monomer and at least one B monomer, Y is chosen from divalent allylene groups, divalent arylene groups, divalent alkarylene groups, and divalent aralkylene groups, wherein the groups comprise from 1 to 30 carbon atoms, and further wherein the groups optionally further comprise at least one group chosen from ester groups, amide groups, urethane groups, and urea groups;

n is zero or 1;

m is a number ranging from 1 to 3;

R, which may be identical or different, are each chosen from hydrogen, $C_1$-$C_4$ alkyl groups, aryl groups, and alkoxy groups; and Z, which may be identical or different, are each chosen from monovalent siloxane polymeric groups; and D, which may be identical or different, are each chosen from free-radically-polymerizable acrylate monomers and free-radically-polymerizable methacrylate monomers. Such polymers and their manufacture are disclosed in U.S. Pat. Nos. 5,209,924 and 4,972,037, and WO 01/32737, the disclosures of which are hereby incorporated by reference.

Further non-limiting examples of the at least one copolymer include polymers comprising at least one A monomer, at least one C monomer, and at least one D monomer, wherein A, which may be identical or different, are each chosen from polymerizable acrylic esters of at least one fluoroalkylsulfonamido alcohol and polymerizable methacrylic esters of at least one fluoroalkylsulfonamido alcohol, D, which may be identical or different, are each chosen from methacrylic acid esters of at least one $C_1$-$C_{12}$ linear alcohol and methacrylic acid esters of at least one $C_1$-$C_{12}$ branched alcohol, and C is as defined above in paragraphs 115 to 123. Such polymers include polymers comprising at least one group of the formula:

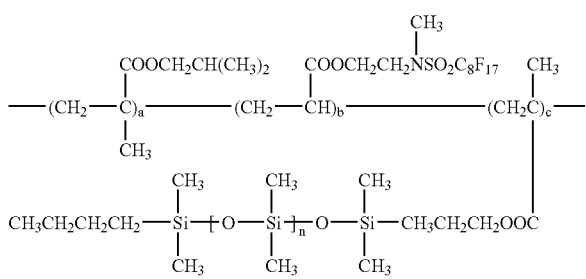

wherein a, b, and c, which may be identical or different, are each a number ranging from 1 to 100,000; and the terminal groups, which may be identical or different, are each chosen from $C_1$-$C_{20}$ linear alkyl groups, $C_3$-$C_{20}$ branched chain alkyl groups, $C_3$-$C_{20}$ aryl groups, $C_1$-$C_{20}$ linear alkoxy groups, and $C_3$-$C_{20}$ branched alkoxy groups.

Such polymers are disclosed in U.S. Pat. Nos. 4,972,037, 5,061,481, 5,209,924, 5,849,275, and 6,033,650, and WO 93/23446 and WO 95/06078. These polymers may be purchased from Minnesota Mining and Manufacturing Company under the tradenames "Silicone Plus" polymers. For example, poly(isobutyl methacrylate-co-methyl perfluorooctane sulfonamido ethyl acrylate)-g-poly (dimethylsiloxane) is sold under the tradename SA 70-5 IBMMF.

Other non-limiting examples of the at least one copolymer is silicone/acrylate graft terpolymers, for example, those having the formula:

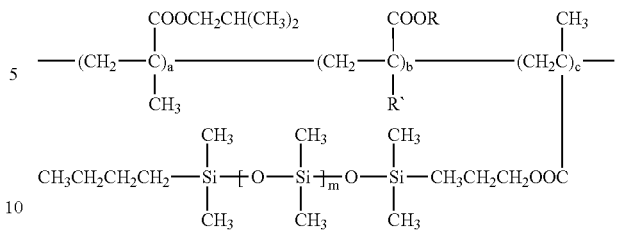

wherein a, b, and c are present in a weight ratio of 69.9:0.1:30 respectively,

R and $R^1$, which may be identical or different, are each chosen from hydrogen and $C_1$-$C_6$ alkyl groups; and m is a number ranging from 100-150.

In an embodiment, m is chosen to provide a macromer having a molecular weight ranging from 8,000 to 12,000, such as 10,000. In another embodiment, m is a number ranging from 124-135, such as 130. Non-limiting examples of these copolymers are described in WO 01/32727 A1, the disclosure of which is hereby incorporated by reference.

In another embodiment of the invention, the at least one copolymer comprises a backbone chosen from vinyl backbones, methacrylic backbones, and acrylic polymeric backbones and further comprises at least one pendant siloxane group. Non-limiting examples of such polymers are disclosed in U.S. Pat. Nos. 4,693,935, 4,981,903, 4,981,902, the disclosures of which are hereby incorporated by reference.

In an embodiment, the at least one copolymer comprises at least one A monomer, at least one C monomer, and, optionally at least one B monomer, wherein the at least one A monomer is chosen from free-radically-polymerizable vinyl monomers, free-radically-polymerizable methacrylate monomers, and free-radically-polymerizable acrylate monomers; the at least one B monomer, if present, is chosen from at least one reinforcing monomer copolymerizable with the at least one A monomer, and the at least one C monomer is chosen from monomers having the formula:

$$X(Y)_nSi(R)_{3-m}Z_m$$

wherein:

X is chosen from vinyl groups which are copolymerizable with the at least one A monomer and with the at least one B monomer;

Y is chosen from divalent groups;

n is zero or 1;

m is a number ranging from 1 to 3;

R, which may be identical or different, are each chosen from hydrogen, optionally substituted $C_1$-$C_{10}$ alkyl groups, optionally substituted phenyl groups, and optionally substituted $C_1$-$C_{10}$ alkoxy groups; and Z, which may be identical or different, are each chosen from monovalent siloxane polymeric groups.

Non-limiting examples of A monomers include methacrylic acid esters of $C_1$-$C_{12}$ linear alcohols, methacrylic acid esters of $C_1$-$C_{12}$ of branched alcohols, styrene monomers, vinyl esters, vinyl chloride monomers, vinylidene chloride monomers, and acryloyl monomers.

Non-limiting examples of B monomers include acrylic monomers comprising at least one group chosen from hydroxyl, amino, and ionic groups, and methacrylic monomers comprising at least one group chosen from hydroxyl, amino, and ionic groups. Non-limiting examples of ionic groups include quaternary ammonium groups, carboxylate salts, and sulfonic acid salts.

The C monomers are as above defined above in paragraphs 115 to 123.

In another embodiment of the invention, the at least one copolymer is chosen from vinyl-silicone graft copolymers having the following formula and vinyl-silicone block copolymers having the following formula:

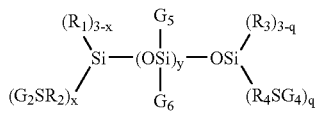

wherein $G_5$, which may be identical or different, are each chosen from alkyl groups, aryl groups, aralkyl groups, alkoxy groups, alkylamino groups, fluoroalkyl groups, hydrogen, and —ZSA groups, wherein
  A is chosen from vinyl polymeric segments comprising at least one polymerized free-radically-polymerizable monomer, and
  Z is chosen from divalent $C_1$-$C_{10}$ alkylene groups, divalent aralkylene groups, divalent arylene groups, and divalent alkoxylalkylene groups. In an embodiment Z is chosen from methylene groups and propylene groups.
$G_6$, which may be identical or different, are each chosen from alkyl groups, aryl groups, aralkyl groups, alkoxy groups, alkylamino groups, fluoroalkyl groups, hydrogen, and —ZSA groups, as defined above;
$G_2$ comprises A;
$G_4$ comprises A;
$R_1$, which may be identical or different, are each chosen from alkyl groups, aryl groups, aralkyl groups, alkoxy groups, alkylamino groups, fluoroalkyl groups, hydrogen, and hydroxyl. In one embodiment, $R_1$ is chosen from $C_1$-$C_4$ alkyl groups, such as methyl groups, and hydroxyl.
$R_2$, which may be identical or different, are each chosen from divalent $C_{1-10}$ alkylene groups, divalent arylene groups, divalent aralkylene groups, and divalent alkoxyalkylene groups. In one embodiment, $R_2$ is chosen from divalent $C_1$-$C_3$ alkylene groups and divalent $D_7$-$C_{10}$ aralkylene groups. In another embodiment, $R_2$ is chosen from —$CH_2$— groups and divalent 1,3-propylene groups.
$R_3$, which may be identical or different, are each chosen from alkyl groups, aryl groups, aralkyl groups alkoxy groups, alkylamino groups, fluoroalkyl groups, hydrogen, and hydroxyl. In one embodiment, $R_3$ is chosen from $C_1$-$C_4$ alkyl groups and hydroxyl. In another embodiment, $R_3$ is chosen from methyl groups.
$R_4$, which may be identical or different, are each chosen from divalent $C_1$-$C_{10}$ alkylene groups, divalent arylene groups, divalent aralkylene groups, and divalent alkoxyalkylene groups. In one embodiment, $R_4$ is chosen from divalent $C_1$-$C_3$ alkylene groups and divalent $C_7$-$C_{10}$ aralkylene groups. In another embodiment, $R_4$ is chosen from divalent —$CH_2$— groups and divalent 1,3-propylene groups.
x is a number ranging from 0 to 3;
y is a number greater than or equal to 5. In an embodiment, y ranges from 10 to 270, and in another embodiment, y ranges from 40 to 270.
q is a number ranging from 0 to 3;

Non-limiting examples of these polymers are described in U.S. Pat. No. 5,468,477, the disclosure of which is hereby incorporated by reference. A non-limiting example of such polymers is poly(dimethylsiloxane)-g-poly(isobutyl methacrylate), which is commercially available from 3M Company under the tradename VS 70 IBM.

In an embodiment, the at least one copolymer is present in the composition in an amount ranging from 0.2% to 30% by weight relative to the total weight of the composition. In another embodiment, the at least one copolymer is present in an amount ranging from 1% to 10% by weight relative to the total weight of the composition. One of ordinary skill in the art will recognize that the at least one copolymer according to the present invention may be commercially available, and may come from suppliers in the form of a dilute solution. The amounts of the at least one copolymer disclosed herein therefore reflect the weight percent of active material.

As previously mentioned, the inventive composition may further comprise at least one wax that is not a compound comprising at least one ester group. At least one wax, for example, may be used to form a non-transparent composition. As used herein, a "wax" may be any lipophilic fatty compound which is soluble in a fatty phase, unlike most fillers or pigments. The at least one wax, for example, may have a melting point greater than about 35° C., such as, for example greater than about 55° C.

Non-limiting examples of waxes, which may or may not be compounds comprising at least one ester group, include waxes of natural origin, such as beeswax, modified beeswax, carnauba wax, candelilla wax, jojoba wax, ouricury wax, Japan wax, cork fiber wax, sugar cane wax, paraffin waxes, lignite wax, microcrystalline waxes, lanolin wax, montan wax and ozokerites, hydrogenated oils such as hydrogenated jojoba oil, jojoba esters, waxes of synthetic origin, such as polyethylene waxes derived from polymerization of ethylene, waxes obtained by Fischer-Tropsch synthesis, fatty acid esters, fatty acid glycerides, and silicone waxes different from the at least one silicone and the at least one copolymer.

In an embodiment, the at least one wax is present in the composition in an amount ranging from 0.1% to 50% by weight relative to the total weight of the composition. In another embodiment, the at least one wax is present in an amount ranging from 5% to 25% by weight relative to the total weight of the composition.

Further, the compositions of the present invention may further comprise at least one coloring agent. The at least one coloring agent may be chosen from pigments, dyes, nacreous pigments, and pearling agents. The at least one coloring agent may be chosen, for example, in order to obtain make-up compositions which give good coverage, that is, which do not leave a significant amount of the at least one keratin material to which it is applied showing through. The at least one coloring agent may also reduce the sticky feel of the compositions, unlike soluble dyes.

Representative liposoluble dyes which may be used according to the present invention include Sudan red, DC Red 17, DC Green 6, β-carotene, soybean oil, Sudan brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%.

The nacreous pigments (or nacreous pigments) which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, may have a concentration ranging up to 50% by weight of the total weight of the composition, such as from 0.1% to 20%.

The pigments which may be used according to the present invention may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate and ferric blue. Representative examples of organic pigments include carbon black, pigments of D & C type, and lakes based on cochineal carmine, barium, strontium, calcium and aluminum. If present, the pigments may have a concentration ranging up to 40% by weight of the total weight of the composition, such as from 1% to 35%, and further such as from 2% to 25%. In the case of certain products, the pigments, including nacreous pigments, may, for example, represent up to 50% by weight of the composition.

In an embodiment of the present invention, the inventive composition comprises at least one pigment. In another embodiment, the at least one pigment is chosen from encapsulated pigments. As used herein, "encapsulated pigments" refer to pigments which are encapsulated within at least one polymer. The capsule may release some of its contents, i.e., the enclosed pigment and dispersing solvent, if present, when pressure is applied to the composition comprising such encapsulated pigments. For example, when encapsulated pigments are comprised in a lip product composition, the capsule may release some of the its contents when the lips are pressed together.

Accordingly, in an embodiment, the inventive compositions comprise at least one encapsulated pigment, wherein the encapsulated pigments are dispersed in at least one solvent. Thus, when pressure is applied to the composition, the capsule may release some of its contents and may thereby allow maintenance of at least one of the color (from the pigments) and the gloss (from the at least one solvent) on the lips. In an embodiment, the at least one solvent is chosen from silicones. In another embodiment, the at least one solvent is chosen from non-volatile silicones. In another embodiment, the at least one solvent is phenyltrimethicone.

Thus, the present invention also provides, in an embodiment, a composition comprising at least one encapsulated pigment, wherein the at least one encapsulated pigment is dispersed in at least one silicone. In another embodiment, the at least one solvent is chosen from non-volatile silicones. In another embodiment, the at least one solvent is chosen from solvents having a refractive index greater than or equal to 1.44 at a temperature ranging from 20° C. to 25° C. In another embodiment, the at least one solvent is chosen from solvents having a refractive index greater than or equal to 1.44 at 20° C. In another embodiment, the at least one solvent is chosen from solvents having a refractive index greater than or equal to 1.44 at 25° C. In another embodiment, the at least one solvent is phenyltrimethicone.

In an embodiment, the invention provides for a composition comprising at least one encapsulated pigment, wherein the at least one encapsulated pigment is dispersed in phenyltrimethicone. In another embodiment, the present invention provides a method for maintaining at least one property chosen from color and gloss of a composition on at least one keratinous material comprising applying a composition comprising at least one encapsulated pigment, wherein the at least one encapsulated pigment is dispersed in at least one silicone. The maintenance of gloss of a composition over time may be measured by, for example, visual inspection after a specific amount of time. For example, gloss is maintained if the gloss of the composition on the keratinous material after 30 minutes after application of the composition to the keratinous material is the equal to or greater than the gloss of the same composition upon application as viewed by the naked eye. The maintenance of color of a composition over time may be measured by, for example, visual inspection after a specific amount of time. For example, color is maintained if the color of the composition on the keratinous material after 30 minutes after application of the composition to the keratinous material is as intense or more intense than the color of the same composition upon application as viewed by the naked eye. Further, L values of the composition can be measured (for example, using Minolta Chroma Meter CR-300) to determine the intensity of the color. In the cosmetic arts, and as defined in the L, a, b colorimetric notations system of the Commission Internationale de l'Eclairage, L defines the intensity of the shade. See U.S. Pat. No. 6,010,541, Col 1, line 66 to Col. 2, line 8, and Col. 9, lines 15-57. The shade is proportionally more intense the lower the value of L (0=black, 100=white). Thus, at least one coloring agent is dispersed if there is an increase in intensity of color, i.e., a decrease in the L value.

Accordingly to the present invention, the inventive compositions may further comprise at least one filler. As used herein, the term "filler" means any particle that is solid at room temperature and atmospheric pressure, used alone or in combination, which does not react chemically with the various ingredients of the composition and which is insoluble in these ingredients, even when these ingredients are raised to a temperature above room temperature and in particular to their softening point or their melting point. In an embodiment, the at least one filler has a melting point at least greater than 170° C., for example, greater than 200° C. In an embodiment, the at least one filler may have an apparent diameter ranging from 0.01 µm to 150 µm, such as from 0.5 µm to 120 µm, for example from 1 µm to 80 µm. An apparent diameter corresponds to the diameter of the circle into which the elementary particle fits along its shortest dimension (thickness for leaflets). Further, the at least one filler may be absorbent, i.e., capable in particular of absorbing the oils of the composition and also the biological substances secreted by the skin, may be surface-treated, e.g., to make it lipophilic, and/or may be porous so as to absorb the sweat and/or sebum secreted by the skin.

The at least one filler may be chosen from inorganic and organic fillers, and may have any shape such as lamellar, spherical and/or oblong. Non-limiting examples of the at least one inert filler include talc, mica, silica, kaolin, polyamide powders (such as Nylon® powder, and such as the product sold by Atochem as Orgasol®), poly-β-alanine powders, polyethylene powders, acrylic polymer powders (such as polymethyl methacrylate (PMMA) powder, for instance the product sold by Wacker as Covabead LH-85 (particle size 10-12 µm) and the acrylic acid copolymer powder sold by Dow Corning as Polytrap®), polytetrafluoroethylene (Teflon®) powders, lauroyllysine, boron nitride, silica, kaolin, starch, starch derivatives, hollow polymer microspheres (such as those hollow polymer microspheres formed from polyvinylidene chloride and acrylonitrile, for instance the product sold by Nobel Industrie as Expancel®), and polymerized silicone microspheres (such as those polymerized silicone microspheres sold by Toshiba as Tospearl®), precipitated calcium carbonate, magnesium carbonate and hydrocarbonate, hydroxyapatite, hollow silica microspheres (such as the product sold by Maprecos as Silica Beads®), glass microcapsules, ceramic microcapsules, and polyester particles.

The at least one filler may be present in the inventive composition in an amount ranging greater than or equal to 0.5% by weight relative to the weight of the total composition, such as from 1% to 20%, and, for example, from 2% to 10%.

The inventive compositions may further comprise at least one solvent. In an embodiment, the at least one solvent is chosen from non-volatile solvents. Non-limiting examples of non-volatile solvents include non-volatile silicones different from the at least one silicone and the at least one copolymer, non-volatile hydrocarbons, and non-volatile alcohols.

Further, the inventive composition may, for example, be a molded composition or cast as a stick or a dish. The inventive composition, in an embodiment, is a solid, such as a molded stick or a poured stick. In another embodiment, the inventive composition is in a form chosen from molded sticks, poured sticks and gels.

The concentrations of the at least one silicone, the at least one ester, the at least one diester, the at least one copolymer, and the at least one wax not chosen from esters or diesters, if present, may be chosen according to the desired hardness and desired stability of the compositions and according to the specific application envisaged. The respective concentrations of the components of the inventive composition can be such that a disintegrable solid which does not flow under its own weight at 25° C. is obtained.

Depending on the intended application, such as a stick, hardness of the composition may also be considered. In an embodiment, the at least one copolymer is present in an amount effective to further provide hardness to the composition. The hardness of a composition may, for example, be expressed in grams (g). The composition of the present invention may, for example, have a hardness ranging from 10 g to 5000 g, such as from 15 g to 500 g, further such as from 20 g to 600 g, and further such as from 30 g to 150 g.

This hardness is measured as follows. A test for hardness is according to a method of penetrating a probe into the composition and in particular using a texture analyzer (for example TA-XT2i from Stable Microsystems) equipped with a stainless steel cylinder of height 35 mm and diameter 4 mm. The hardness measurement is carried out at 20° C. at the center of 5 samples of the composition. The cylinder penetrates at a speed of 2 mm/s, the total displacement being 5 mm. The recorded hardness value is that of the maximum peak observed. The measurement error is ±10 g.

The hardness of the composition of the present invention may be such that the compositions are self-supporting and can easily disintegrate to form a satisfactory deposit on a keratinous material. In addition, this hardness may impart good impact strength to the inventive compositions which may be molded or cast, for example, in stick or dish form.

The skilled artisan may choose to evaluate a composition using the tests for hardness outlined above based on the application envisaged and the hardness desired.

According to the present invention, the compositions in stick form may also possess the properties of deformable, flexible elastic solids and may also have noteworthy elastic softness upon application to a keratinous material. Further, in an embodiment, the inventive composition has a melting point ranging from 40° C. to 150° C.

The composition of the present invention may also further comprise at least one suitable additive commonly used in the field concerned chosen from fatty materials, coloring agents, fillers, humectants, texture modifiers, antifoaming agents, moisturizers, viscosity modifiers, antioxidants, essential oils, preserving agents, fragrances, neutralizing agents, liposoluble polymers, polysaccharides, fluorinated compounds, and cosmetically active agents and dermatological active agents such as, for example, emollients, vitamins, plant extracts, essential fatty acids and UV-screening agents. In an embodiment, the composition of the present invention is transparent and/or clear, including, for example, a composition without pigments. In yet another embodiment, the composition of the present invention is neither transparent nor clear.

Needless to say, the person skilled in the art will take care to select the optional additional additives and the amount thereof such that at least one advantageous property of the composition according to the invention, such as stability, non-migration, is not, or is not substantially, adversely affected by the addition(s) envisaged.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and in the attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result. The percentages are given on a weight basis.

EXAMPLE 1

The following compositions were prepared.

TABLE 1

| Components | Composition 1 (% wt) | Composition 2 (% wt) | Composition 3 (% wt) |
|---|---|---|---|
| Hydrogenated polyisobutene | 6.00 | 6.00 | 6.00 |
| Isononyl isonananoate | 14.00 | 15.48 | 14.00 |
| Phenyltrimethicone | 10.00 | 10.00 | 10.00 |
| Diisostearyl malate | 22.63 | 22.14 | 22.63 |

TABLE 1-continued

| Components | Composition 1 (% wt) | Composition 2 (% wt) | Composition 3 (% wt) |
|---|---|---|---|
| Dipentaerythrityl tetrahydroxy stearate/isostearate | 7.00 | 7.00 | 7.00 |
| Stearyl Heptanoate | 3.00 | 1.02 | 4.00 |
| Acrylates/stearyl acrylated/dimethicone acrylated copolymer* | 4.00 | 4.00 | 4.00 |
| Trimethylsiloxysilicate | 5.00 | 5.00 | 5.00 |
| BHT | 0.05 | 0.05 | 0.05 |
| Waxes | 16.00 | 16.50 | 16.00 |
| Pigments | 3.70 | 3.11 | 3.70 |
| Encapsulated pigments in Phenyltrimethicone | 1.00 | 5.00 | — |
| Fillers | 6.42 | 3.70 | 6.42 |
| Antifoam | 0.20 | 0.20 | 0.2 |
| Vitamins and plant extracts | 1.00 | 0.80 | 1.00 |

*KP561 from Shin-Etsu

Preparation

Hydrogenated polyisobutene, isononyl isononanoate, phenyltrimethicone, and the excess over 15% of diisostearyl malate were added to a mixing kettle and the mixture was heated to 90° C. to 95° C. under medium agitation. Stearyl heptanoate was then added to the mixing kettle, and the resulting mixture was mixed until homogeneous at 90° C. to 95° C. One by one dipentaerythrityl tetrahydroxy stearate/isostearate, acrylates/stearyl acrylated/dimethicone acrylated copolymer and trimethylsiloxysilicate (SR1000) were added to the mixture, ensuring that each individual component was melted and homogeneous. The resulting mixture was mixed for another 20 minutes at 90° C. to 95° C. Finally, BHT was added, and the resulting mixture was mixed for 20 minutes at 90° C. to 95° C.

The mixture was then placed into a mill and was heated to 60° C. to 65° C. Non-encapsulated pigments were added to the mixture, and the resulting mixture was milled at 60° C. to 65° C. for 40 to 45 minutes. Once the mixture was well dispersed, the waxes were added to the mixture with stirring. The mixture was then heated to 110° C. to 115° C. until the waxes were melted.

The mixture was then discharged from the mill, transferred to a mixing kettle and heated to 90° C. to 95° C. The mill was rinsed with the remaining diisostearyl malate (15% by weight) for 20 to 30 minutes. This portion of diisostearyl malate was then also added to the mixing kettle. If present, the encapsulated pigments, pre-dispersed in isononyl nonanoate in a Silverson homogenizer, are added to the mixture in the mixing kettle. The mixture was heated until uniform. Fillers were then added to the mixture with stirring until uniform, followed by the antifoam. The mixture was stirred for 20 to 30 minutes with medium agitation.

The temperature was lowering to 80° C. and the vitamins and plant extracts were added. The mixture was mixed to an additional 10 to 15 minutes, and then poured into a mold.

EXAMPLE 2

The following compositions were prepared according to the above method.

TABLE 2

| Components | Composition 4 (% wt) | Composition 5 (% wt) |
|---|---|---|
| Hydrogenated polyisobutene | 6.20 | 6.20 |
| Isononyl isonananoate | 14.64 | 14.64 |
| Phenyltrimethicone | 12.40 | 12.40 |
| Diisostearyl malate | 22.80 | 22.80 |
| Dipentaerythrityl tetrahydroxy stearate/isostearate | 6.40 | 7.40 |
| Stearyl Heptanoate | 2.50 | 2.50 |
| Acrylates/stearyl acrylated/dimethicone acrylated copolymer* | 4.00 | 4.00 |
| Trimethylsioxysilicate | 5.00 | 5.00 |
| BHT | 0.05 | 0.05 |
| Waxes | 14.20 | 14.20 |
| Pigments | 8.41 | 8.41 |
| Antifoam | 0.20 | 0.20 |
| Fillers | 1.20 | 1.20 |
| Cholesteryl/behenyl/octododecyl lauroyl glutamate | 1.00 | — |
| Vitamins and plant extracts | 1.00 | 1.00 |

*KP561 from Shin-Etsu

What is claimed is:

1. A composition comprising:
   (a) at least one compound comprising at least one ester group;
   (b) at least one silicone; and
   (c) at least one copolymer comprising at least one backbone and at least one chain, wherein at least one of said at least one backbone and at least one chain is chosen from silicones;
   with the proviso that said composition comprises no volatile solvents, and wherein said at least one copolymer is chosen from acrylates/stearyl acrylate/dimethicone acrylates copolymers and acrylates/behenyl acrylate/dimethicone acrylates copolymers.

2. The composition according to claim 1, wherein said at least one copolymer is present in said composition in an amount ranging from 0.2% to 30% by weight relative to the total weight of said composition.

3. The composition according to claim 1, wherein said at least one silicone is chosen from dimethicones, trimethicones, polyalkyl siloxanes, polyaryl siloxanes, polyalkylaryl siloxanes, polyether siloxane copolymers, alkylaryl-diaryl siloxane copolymers, dimethiconols, polydialkylsiloxane/alkylvinylsiloxane copolymers, (polydialkylsiloxane)(diphenyl)(methylvinylsiloxane) copolymers, and siloxysilicates; and wherein said at least one silicone is present in an amount ranging from 0.5% to 20% by weight relative to the total weight of said composition.

4. The composition according to claim 1, wherein said at least one compound comprising at least one ester group is chosen from esters and diesters: wherein said diesters are chosen from diesters of formula (I):

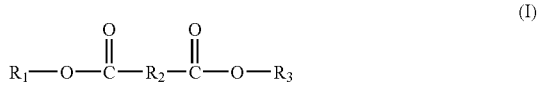

and diesters of the following formula:

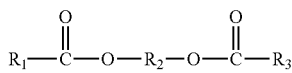

wherein
R$_1$ and R$_3$, which may be identical or different, are each chosen from
optionally substituted hydrocarbon groups; and
R$_2$ is chosen from optionally substituted, divalent hydrocarbon groups; and wherein said esters are chosen from esters of formula (II):

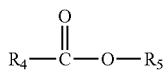 (II)

wherein
R$_4$ and R$_5$, which may be identical or different, are each chosen from unsubstituted hydrocarbon groups, wherein said hydrocarbon groups each comprise at least four carbon atoms,
and esters of the following formula:

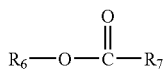

wherein
R$_6$ and R$_7$, which may be identical or different, are each chosen from optionally substituted hydrocarbon groups; and
wherein said at least one compound comprising at least one ester group is present in said composition in an amount ranging from 1% to 80% by weight relative to the total weight of said composition.

5. The composition according to claim 1, wherein said at least one compound comprising at least one ester group is chosen from diglycerol diisostearate, PEG distearates, diisostearyl malate, butyl heptanoate, butyl laurate, butyl isononanoate, butyl myristate, butyl octanoate, butyl oleate, butyl palmitate, butyl stearate, cetyl heptanoate, cetyl laurate, cetyl isononanoate, cetyl myristate, cetyl octanoate, cetyl oleate, cetyl palmitate, cetyl stearate, isononyl heptanoate, isononyl laurate, isononyl isononanoate, isononyl myristate, isononyl octanoate, isononyl oleate, isononyl palmitate, isononyl stearate, hexyl heptanoate, hexyl laurate, hexyl isononanoate, hexyl myristate, hexyl octanoate, hexyl oleate, hexyl palmitate, hexyl stearate, isostearyl heptanoate, isostearyl isostearate, isostearyl neopentanoate, isostearyl isononanoate, lauryl heptanoate, lauryl isononanoate, lauryl myristate, lauryl octanoate, lauryl oleate, lauryl palmitate, lauryl stearate, stearyl heptanoate, stearyl laurate, stearyl isononanoate, stearyl myristate, stearyl octanoate, stearyl oleate, stearyl palmitate, stearyl stearate, and waxes.

6. The composition according to claim 1, wherein said composition is a cosmetic composition that further comprises at least one wax, at least one coloring agent, at least one additive, or a combination thereof.

7. A composition comprising:
(a) at least one compound comprising at least one ester group;
(b) at least one silicone; and
(c) at least one copolymer comprising at least one backbone and at least one chain, wherein at least one of said at least one backbone and at least one chain is chosen from silicones;
with the proviso that said composition comprises no volatile solvents, and wherein said at least one copolymer is chosen from polymers comprising at least one unit derived from at least one A monomer, at least one unit derived from at least one C monomer, at least one unit derived from D monomers, and, optionally, at least one unit derived from at least one B monomer, wherein:
A, which may be identical or different, are each chosen from free-radically-polymerizable acrylic esters of at least one alcohol chosen from 1,1,-dihydroperfluoroalkanols, omega-hydridofluoroalkanols, fluoroalkylsulfonamido alcohols, cyclic fluoroalkyl alcohols, and fluoroether alcohols, and free-radically-polymerizable methacrylic esters of at least one alcohol chosen from 1,1,-dihydroperfluoroalkanols, omega-hydridofluoroalkanols, fluoroalkylsulfonamido alcohols, cyclic fluoroalkyl alcohols, and fluoroether alcohols;
B, which may be identical or different, are each chosen from reinforcing monomers which are copolymerizable with at least one A monomer;
C, which may be identical or different, are each chosen from monomers having the formula:

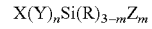

wherein
X is chosen from vinyl groups which are copolymerizable with at least one A monomer and at least one B monomer,
Y is chosen from divalent allylene groups, divalent arylene groups, divalent alkarylene groups, and divalent aralkylene groups, wherein the groups comprise from 1 to 30 carbon atoms, and further wherein the groups optionally further comprise at least one group chosen from ester groups, amide groups, urethane groups, and urea groups;
n is zero or 1;
m is a number ranging from 1 to 3;
R, which may be identical or different, are each chosen from hydrogen, C$_1$-C$_4$ alkyl groups, aryl groups, and alkoxy groups; and
Z, which may be identical or different, are each chosen from monovalent siloxane polymeric groups; and
D, which may be identical or different, are each chosen from free-radically-polymerizable acrylate monomers and free-radically-polymerizable methacrylate monomers.

8. The composition according to claim 7, wherein said at least one copolymer is present in said composition in an amount ranging from 0.2% to 30% by weight relative to the total weight of said composition.

9. The composition according to claim 7, wherein said at least one silicone is chosen from dimethicones, trimethicones, polyalkyl siloxanes, polyaryl siloxanes, polyalkylaryl siloxanes, polyether siloxane copolymers, alkylaryl diaryl siloxane copolymers, dimethiconols, polydialkylsiloxane/alkylvinylsiloxane copolymers, (polydialkylsiloxane)(diphenyl)(methylvinylsiloxane) copolymers, and siloxysilicates; and wherein said at least one silicone is present in an amount ranging from 0.5% to 20% by weight relative to the total weight of said composition.

10. The composition according to claim 7, wherein said at least one compound comprising at least one ester group is chosen from esters and diesters: wherein said diesters are chosen from
diesters of formula (I):

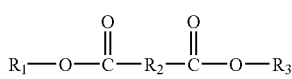

and diesters of the following formula:

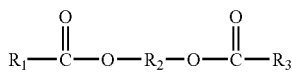

wherein
$R_1$ and $R_3$, which may be identical or different, are each chosen from optionally substituted hydrocarbon groups; and
$R_2$ is chosen from optionally substituted, divalent hydrocarbon groups; and wherein said esters are chosen from esters of formula (II):

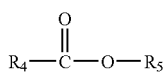

wherein
$R_4$ and $R_5$, which may be identical or different, are each chosen from unsubstituted hydrocarbon groups, wherein said hydrocarbon groups each comprise at least four carbon atoms,
and esters of the following formula;

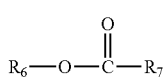

wherein
$R_6$ and $R_7$, which may be identical or different, are each chosen from optionally substituted hydrocarbon groups; and
wherein said at least one compound comprising at least one ester group is present in said composition in an amount ranging from 1% to 80% by weight relative to the total weight of said composition.

11. The composition according to claim 7, wherein said at least one compound comprising at least one ester group is chosen from diglycerol diisostearate, PEG distearates, diisostearyl malate, butyl heptanoate, butyl laurate, butyl isononanoate, butyl myristate, butyl octanoate, butyl oleate, butyl palmitate, butyl stearate, cetyl heptanoate, cetyl laurate, cetyl isononanoate, cetyl myristate, cetyl octanoate, cetyl oleate, cetyl palmitate, cetyl stearate, isononyl heptanoate, isononyl laurate, isononyl isononanoate, isononyl myristate, isononyl octanoate, isononyl oleate, isononyl palmitate, isononyl stearate, hexyl heptanoate, hexyl laurate, hexyl isononanoate, hexyl myristate, hexyl octanoate, hexyl oleate, hexyl palmitate, hexyl stearate, isostearyl heptanoate, isostearyl isostearate, isostearyl neopentanoate, isostearyl isononanoate, lauryl heptanoate, lauryl isononanoate, lauryl myristate, lauryl octanoate, lauryl oleate, lauryl palmitate, lauryl stearate, stearyl heptanoate, stearyl laurate, stearyl isononanoate, stearyl myristate, stearyl octanoate, stearyl oleate, stearyl palmitate, stearyl stearate, and waxes.

12. The composition according to claim 7, wherein said composition is a cosmetic composition that further comprises at least one wax, at least one coloring agent, at least one additive, or a combination thereof.

13. A composition comprising:
(a) at least one compound comprising at least one ester group;
(b) at least one silicone; and
(c) at least one copolymer comprising at least one backbone and at least one chain, wherein at least one of said at least one backbone and at least one chain is chosen from silicones;
with the proviso that said composition comprises no volatile solvents, and wherein said at least one copolymer is chosen from polymers comprising at least one A monomer, at least one C monomer, and at least one D monomer, wherein
A, which may be identical or different, are each chosen from polymerizable acrylic esters of at least one fluoroalkylsulfonamido alcohol and polymerizable methacrylic esters of at least one fluoroalkylsulfonamido alcohol;
D, which may be identical or different, are each chosen from methacrylic acid esters of at least one $C_1$-$C_{12}$ linear alcohol and methacrylic acid esters of at least one $C_1$-$C_{12}$ branched alcohol; and
C, which may be identical or different, are each chosen from monomers having the formula:

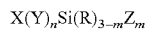

wherein
X is chosen from vinyl groups which are copolymerizable with at least one A monomer and at least one B monomer,
Y is chosen from divalent allylene groups, divalent arylene groups, divalent alkarylene groups, and divalent aralkylene groups, wherein the groups comprise from 1 to 30 carbon atoms, and further wherein the groups optionally further comprise at least one group chosen from ester groups, amide groups, urethane groups, and urea groups;
n is zero or 1;
m is a number ranging from 1 to 3;
R, which may be identical or different, are each chosen from hydrogen, $C_1$-$C_4$ alkyl groups, aryl groups, and alkoxy groups; and
Z, which may be identical or different, are each chosen from monovalent siloxane polymeric groups.

14. The composition according to claim 13, wherein said at least one copolymer is present in said composition in an amount ranging from 0.2% to 30% by weight relative to the total weight of said composition.

15. The composition according to claim 13, wherein said at least one silicone is chosen from dimethicones, trimethicones, polyalkyl siloxanes, polyaryl siloxanes, polyalkylaryl siloxanes, polyether siloxane copolymers, alkylaryl-diaryl siloxane copolymers, dimethiconols, polydialkylsiloxane/alkylvinylsiloxane copolymers, (polydialkylsiloxane)(diphenyl)(methylvinylsiloxane) copolymers, and siloxysilicates; and wherein said at least one silicone is present in an amount ranging from 0.5% to 20% by weight relative to the total weight of said composition.

16. The composition according to claim 13, wherein said at least one compound comprising at least one ester group is chosen from esters and diesters: wherein said diesters are chosen from diesters of formula (I):

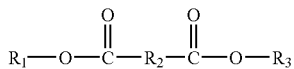
(I)

and diesters of the following formula:

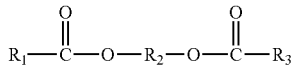

wherein $R_1$ and $R_3$, which may be identical or different, are each chosen from optionally substituted hydrocarbon groups; and $R_2$ is chosen from optionally substituted, divalent hydrocarbon groups; and wherein said esters are chosen from esters of formula (II):

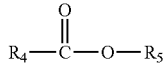
(II)

wherein $R_4$ and $R_5$, which may be identical or different, are each chosen from unsubstituted hydrocarbon groups, wherein said hydrocarbon groups each comprise at least four carbon atoms, and esters of the following formula:

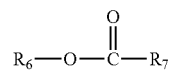

wherein $R_6$ and $R_7$, which may be identical or different, are each chosen from optionally substituted hydrocarbon groups; and wherein said at least one compound comprising at least one ester group is present in said composition in an amount ranging from 1% to 80% by weight relative to the total weight of said composition.

17. The composition according to claim 13, wherein said composition is a cosmetic composition that further comprises at least one wax, at least one coloring agent, at least one additive, or a combination thereof.

18. A composition comprising:
   (a) at least one compound comprising at least one ester group;
   (b) at least one silicone; and
   (c) at least one copolymer comprising at least one backbone and at least one chain, wherein at least one of said at least one backbone and at least one chain is chosen from silicones;
   wherein said at least one copolymer is chosen from diisostearoyl trimethylolpropane siloxysilicate and dilauroyl trimethylolpropane siloxy silicate;
   with the proviso that said composition comprises no volatile solvents, wherein a volatile solvent is a solvent that is an aqueous or nonaqueous medium which is liquid at room temperature (25° C.) and at atmospheric pressure (760 mmHg) and which has a vapor pressure greater than 2 mmHg (at room temperature and atmospheric pressure), and wherein said at least one copolymer is chosen from liquid siloxy silicates and silicone esters.

* * * * *

UNITED STATES PATENT AND TRADEMARK OFFICE
CERTIFICATE OF CORRECTION

PATENT NO.       : 7,311,899 B2
APPLICATION NO.  : 10/356523
DATED            : December 25, 2007
INVENTOR(S)      : Wei Yu It is certified that error appears in the above-identified patent and that said Letters Patent is hereby corrected as shown below:

In claim 10, column 27, line 38, "tour" should read --four--.

In claim 18, column 30, line 37, "pressure)," should read --pressure).--.

In claim 18, column 30, lines 37-39, delete "and wherein said at least one copolymer is chosen from liquid siloxy silicates and silicone esters.".

Signed and Sealed this

Twenty-second Day of July, 2008

JON W. DUDAS
*Director of the United States Patent and Trademark Office*